United States Patent [19]

Lindner et al.

[11] Patent Number: 5,322,510
[45] Date of Patent: Jun. 21, 1994

[54] INJECTION APPARATUS

[75] Inventors: Andreas Lindner, Ungererstr. 65, 8000 Munenchen; Ingolf M. Wechler, Grabenstätt, both of Fed. Rep. of Germany

[73] Assignee: Andreas Lindner, Fed. Rep. of Germany

[21] Appl. No.: 730,861

[22] PCT Filed: Nov. 17, 1990

[86] PCT No.: PCT/DE90/00892
§ 371 Date: Sep. 19, 1991
§ 102(e) Date: Sep. 19, 1991

[87] PCT Pub. No.: WO91/07197
PCT Pub. Date: May 30, 1991

[30] Foreign Application Priority Data

Nov. 21, 1989 [DE] Fed. Rep. of Germany ... 8913761[U]
Jan. 3, 1990 [DE] Fed. Rep. of Germany ... 900024[U]
Mar. 23, 1990 [DE] Fed. Rep. of Germany ... 9003433[U]
Aug. 9, 1990 [DE] Fed. Rep. of Germany ....... 4025503

[51] Int. Cl.$^5$ .............................................. A61M 5/00
[52] U.S. Cl. ...................................... 604/82; 604/83; 604/173; 604/258; 604/280; 239/423
[58] Field of Search .............. 604/82, 83, 173, 258, 604/264, 272, 280; 239/398, 423

[56] References Cited

U.S. PATENT DOCUMENTS 3,223,083 12/1965 Cobey .
3,828,980 8/1974 Creighton et al. ............... 604/82 X
4,040,420 8/1977 Speer ................................ 604/272 X
4,359,049 11/1982 Redl et al. ......................... 604/82
4,631,055 12/1986 Redl et al. ......................... 604/82
4,874,368 10/1989 Miller et al. ....................... 604/82
4,978,336 12/1990 Capozzi et al. ................. 604/191 X
5,116,315 5/1992 Capozzi et al. ................. 239/398 X

FOREIGN PATENT DOCUMENTS 682276 8/1979 U.S.S.R. ............................ 239/423

Primary Examiner—Randall L. Green
Assistant Examiner—Mary Beth Jones
Attorney, Agent, or Firm—Hill, Steadman & Simpson

[57] ABSTRACT

Injection apparatus for injecting at least two components to be brought into reaction with one another, comprising a hollow injection needle that can be charged by a plurality of syringe coupling connections corresponding in number to the number of components, preferably for endoscopic purposes and fashioned displaceable in a catheter on the basis of a grip member, whereby the syringe coupling connections are provided at the catheter in this case, characterized in that the components can be supplied to the injection needle (3) through a corresponding plurality of hoses (4, 5; 17) preferably proceeding through the catheter (1) and respectively connected to one of the syringe coupling connections (6, 7) in the grip member (2), whereby the components discharge in a common plane (30) wherein the reaction of the components is initiated.

8 Claims, 4 Drawing Sheets

INJECTION APPARATUS

BACKGROUND OF THE INVENTION

1. Field of the Invention

The invention is directed to an injection apparatus for injecting at least two components to be brought into reaction with one another, the apparatus including a hollow injection needle that can be coupled to a plurality of syringe coupling connections corresponding in number to the number of components. The apparatus is preferably used for endoscopic purposes and is displaceable in a catheter with a grip member, whereby the syringe coupling connections are provided on the catheter in this case.

2. Description of the Related Art

Such injection apparatus are particularly employed for injecting two-component fibrin adhesives, whereby fibrin or fibrinogen is to be brought into reaction with thrombin at such locations within the human body whereat bleeding must be stopped by closing blood vessels.

Such fibrin adhesive injection apparatus are commercially known and can be divided into two types. In the one type, the hollow injection needle is connected to a hose that discharges into the handle sections of a chamber into which the channels of the two syringe coupling connections in turn discharge. By actuating the two syringes, the two components of the fibrin adhesive are simultaneously introduced into the chamber and from the latter into the hose in which they should mix before they reach the hollow injection needle. On the one hand, a thorough blending of the two components is thereby not guaranteed; on the other hand, there is also the risk that the mixture of components will harden before reaching the hollow injection needle and thereby block the hose. In the other type of apparatus, two hollow injection needles are therefore employed that are bonded to one another side-by-side and are each respectively connected to the syringe coupling connections via a hose, whereby the two hoses proceed side-by-side in the catheter. A relatively large thickness of the composite needles in the directions of their diagonals which continue one another thereby derives, whereby the individual hollow needles have their side containing their tip arranged against one another, so that the aperture angle of the hollow needle arrangement is relatively large, this leading to an undesirably pronounced damage to the tissue. Moreover, a good blending of the two adhesive components is not guaranteed because the components emerge laterally side-by-side from the injection needles into the tissue to be treated and the axes of their discharge flows are at a relatively great distance from one another.

SUMMARY OF THE INVENTION

It is therefore the object of the invention to provide an injection apparatus of the type initially cited, whereby the puncture resistance of the hollow injection needle is kept low and a good blending of the components without risk of premature hardening is achieved.

In an injection apparatus of this type, this object is achieved by the components being supplied to the injection needle through a corresponding plurality of hoses preferably proceeding through the catheter and each respectively connected to one of the syringe coupling connections in the gripping member, the components discharging in a common plane in which the reaction of the components is initiated. Advantageous developments of the invention provided by the hollow injection needle being connected to a first hose wherein a second hose having a smaller outside diameter than the inside diameter of the first hose proceeds coaxially therein up to the grip member, the second hose discharging at a slight distance preceding the proximal end of the hollow injection needle. The injection apparatus may further be characterized in that the injection needle is fixed to a sleeve secured in the first hose, the second hose ending in the sleeve.

It is also contemplated that the injection apparatus include a plurality of injection channels corresponding in number to the number of components, the injection channels being formed in the hollow injection needle and discharging in the end plane of the injection needle. This injection apparatus is then preferable includes a first injection channel connected to a first hose wherein a second hose that is connected to a second injection channel and has a smaller outside diameter than the inside diameter of the first hose proceeds up to the grip member. As a further improvement, the injection apparatus includes an axially proceeding partition in the hollow injection needle and the two injection channels proceeding at the two sides of the partition.

An injection apparatus of the type first described is further characterized in that the hollow injection needle is formed of a plurality of individual hollow needles corresponding in number to the number of components, the end planes of these individual hollow needles lying in a common plane. A preferred embodiment of such apparatus has the individual hollow needles being of different diameters.

The injection apparatus may have the individual hollow needles joined to one another in parallel, or the individual hollow needles are at least partially flattened at their outside and are attached to one another along these flat sides. The individual hollow needles are attached to one another such that the tip of the needle of the hollow injection needle is formed by the tip of the individual hollow needle having the smallest diameter. At least one channel-shaped outwardly arced portion wherein a further individual hollow needle is introduced is fashioned along at least one of the individual hollow needles. The injection apparatus is also characterized in that the individual hollow needles are arranged coaxially relative to one another.

In the invention, the components are supplied to the injection needle through a corresponding plurality of hoses proceeding through the catheter that are each respectively connected to one of the syringe coupling connections in the gripping member, whereby the components discharge in a common plane wherein the reaction of the components is initiated.

In a preferred embodiment, the hollow injection needle is connected to a first hose wherein a second hose having a smaller outside diameter than the inside diameter of the first hose proceeds coaxially therein up to the gripping member, whereby the second hose discharges at a slight distance preceding the proximal end of the hollow injection needle.

It is also preferred that the injection needle is fixed to a sleeve secured in the first hose, the second hose ending in the sleeve.

A plurality of injection channels corresponding in number to the number of components are provided in the hollow injection needle, whereby the injection channels discharge at the end plane of the injection needle.

A first injection channel is thereby again connected to a first hose wherein a second hose that is connected to a second injection channel and has a smaller outside diameter than the inside diameter of the first hose proceeding up to the gripping member.

According to a preferred embodiment, an axially proceeding partition is fashioned in the hollow injection needle and the two injection needles proceed at the two sides of the partition.

Further, the hollow injection needle is formed of a plurality of individual hollow needles corresponding in number to the number of components, the end planes or faces of these individual hollow needles lying in a common plane.

The individual hollow needles thereby have different diameters.

The individual hollow needles also are attached such to one another that the needle tip of the hollow injection needle is formed by the tip of the individual hollow needle having the smallest diameter.

Further, at least one channel-shaped bulged portion wherein a further individual hollow needle is introduced proceeds along at least one of the individual hollow needles.

Finally, a coaxial arrangement of the individual hollow needles is possible.

In the invention, a single end plane of the injection hollow needles is provided for the injection means, regardless of the way in which the delivery of the components occurs. It has been shown that the tissue resistance given an angle of approximately 20% for the end plane relative to the axis of the hollow injection needle remains so low that an excessive damage to the tissue is largely impossible. Such an optimum, uniform angle is retained in every embodiment of the injection means of the invention. It is also defined at the same time that the delivered components discharge in a common plane, whereby the reaction of the components is initiated in this plane. The common plane can lie in one of the hoses preceding the injection needle; however, it can also coincide with the end plane of the injection needle.

BRIEF DESCRIPTION OF THE DRAWINGS

The invention shall be set forth in greater detail below with reference to the drawings merely by way of example. Shown are.

DETAILED DESCRIPTION OF THE PREFERRED EMBODIMENTS

Figure 1:
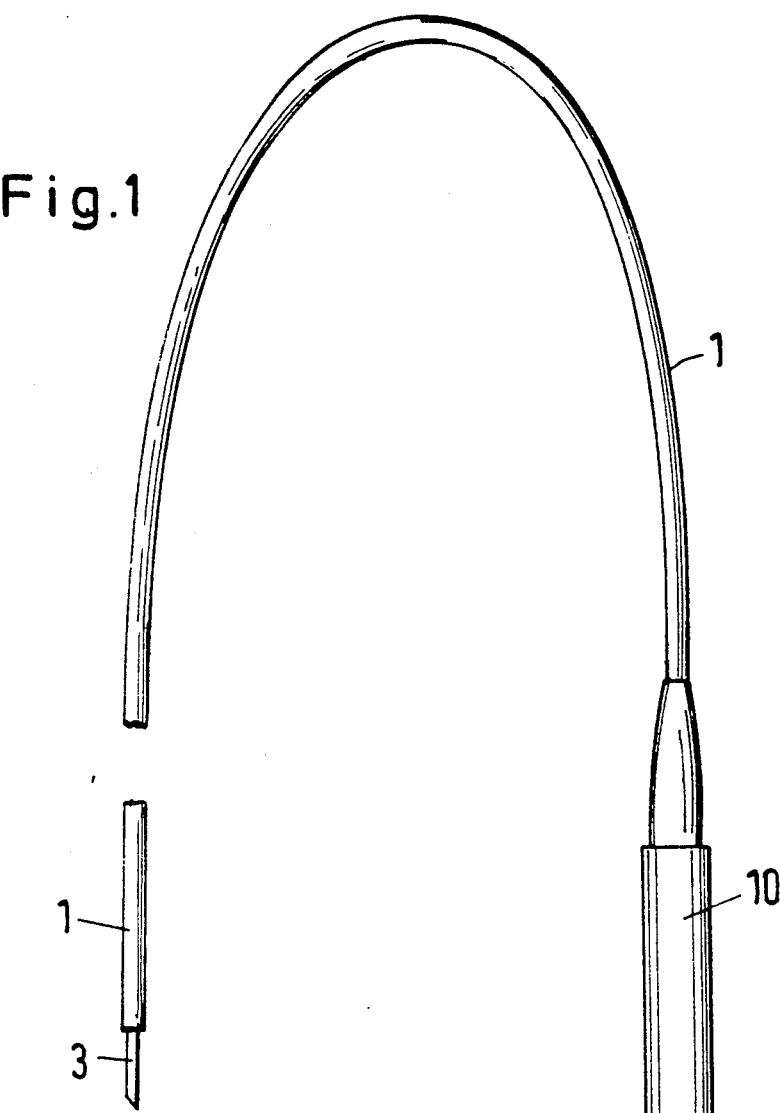
FIG. 1 a side view of the injection means of the invention.

The injection apparatus shown in FIG. 1 comprises a T-shaped grip member 2 that is slipped over a slide sleeve 9 secured to it in a grip sleeve 10 to whose end facing away from the grip member 2 a flexible, hose-shaped catheter 1 is fixed. A hollow injection needle 3 is displaceable in the distal end of the catheter 1 by displacing the slide sleeve 9 in the grip sleeve 10. By pushing the slide sleeve 9 into the grip sleeve 10, thus, the hollow injection needle 3 is pushed out of the distal end of the catheter 1.

Figure 2:
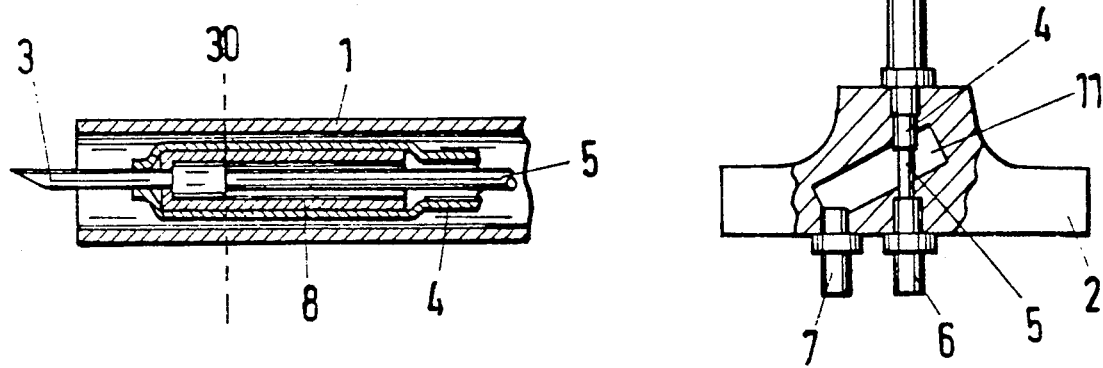
FIG. 2 a partial longitudinal section through a first embodiment of the invention in the region of the hollow injection needle, shown in an enlarged scale.

According to FIG. 2, the injection needle 3 is lengthened by a sleeve 8 for this purpose, the distal end of a first hose 4 whose proximal end is anchored in the gripping member 2 being secured to this sleeve 8. The distal end of a second inside hose 5 discharges freely into the sleeve 8, the outside diameter of this second inside hose 5 being smaller than the inside diameter of the outer hose 2 and proceeding coaxially in the latter up to the grip member 2. At this location, the inner hose 5 is connected to a first syringe coupling connection, by contrast whereto the outer hose discharges into a transverse chamber 11 through which the first hose 4 passes and in which a second syringe coupling connection 7 discharges.

The syringes (not shown) are filled with the adhesive components that, after the syringes have been coupled to the syringe coupling connections 6 and 7 given simultaneous actuation of the syringe piston, are pumped into the respectively allocated hose 4, 5 and meet intimately in a common plane 30 in the sleeve at a distance in front of the hollow injection needle 3 where the reaction of the components is initiated and being blended with one another subsequently until they emerge from the hollow injection needle 3. The initiation of the reaction and the blending ensues immediately in front of the hollow injection needle and in this needle itself, as a result whereof a premature curing of the components is avoided and a blending is nonetheless achieved before emergence from the hollow injection needle into the tissue to be treated. The single-channel hollow injection needle can be adequately thin, as a result whereof no complications can occur upon injection of the component mix.

Figure 3:
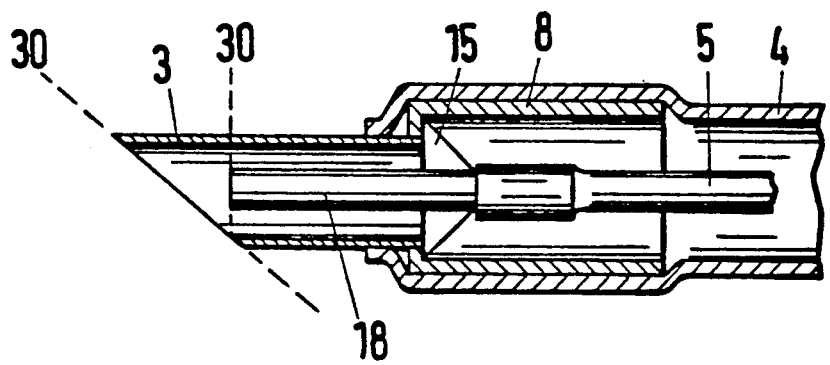
FIG. 3 a partial longitudinal section through a second embodiment of the invention in the region of the hollow injection needle.

In the embodiment of FIG. 3, too, the hollow injection needle 3 is lengthened by a sleeve 8 to which the distal end of a first hose 4 is fixed, the proximal end of this first hose 4 being anchored in the grip member 2. A tube 18 is introduced into the hollow injection needle 3, the distal end of a second inner hose 5 whose outside diameter is smaller than the inside diameter of the outer hose 2 and that proceeds in the latter practically coaxially up to the grip member 2 discharging into this tube 18. The inner hose 5 is again connected to a first syringe coupling connector 6; by contrast thereto, the outer hose discharges into a transverse chamber 11, as set forth in conjunction with FIG. 2. The tube 18 is arranged concentrically relative to the injection needle 3 and is fixed for this purpose in the hose 8 with supporting mechanisms 15. The tube 18 ends at a slight distance before the discharge of the injection needle, whereby the reaction of the components delivered through the hoses 4, 5 is initiated in a plane 30.

Embodiments (not shown) are also possible wherein the tube projects eccentrically into the hollow injection needle or is bonded thereto at one side. The tube can even be merely loosely introduced into the hollow injection needle. Which of the disclosed embodiments is selected also depends on the relative viscosity that the components to be mixed with one another have. Given employment as a fibrin adhesive injection means, one must note that fibrinogen is more viscous and therefore has a higher viscosity than the thrombin, so that an optimally large, uniform flow cross section must be available for the fibrinogen.

Figure 4:
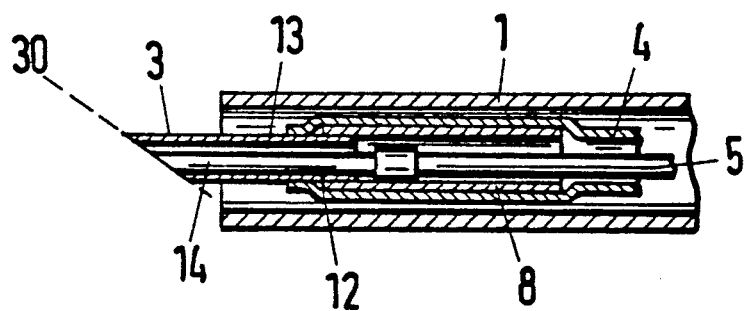
FIG. 4 a partial longitudinal section through a third embodiment of the invention in the region of the hollow injection needle, whereby the hollow injection needle comprises injection channels.

Two injection channels 13 and 14 are provided in FIG. 4 by inserting a hollow needle 12 into the hollow injection needle 3. A hollow needle 12 thereby proceeds eccentrically in the hollow injection needle 3 and can be bonded thereto at one side. Its discharge terminates flush with the ground plane 30 of the hollow injection needle 3. The hollow needle 12 discharges into the distal end of the inner hose 5 that again proceeds roughly coaxially in the hose 4. The injection needle 3 is lengthened by the sleeve 8 and lies in the catheter 1 together with this sleeve 8.

Figure 5:
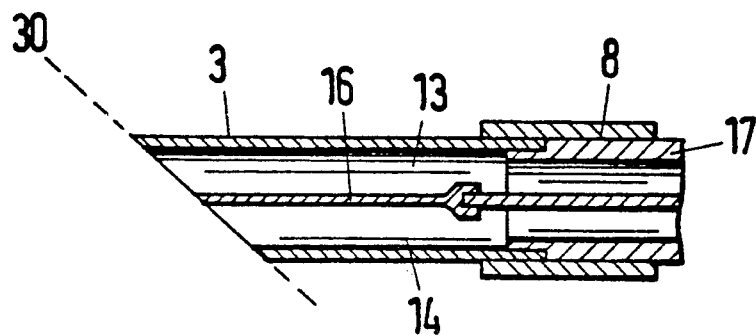
FIG. 5 a partial longitudinal section through a fourth embodiment of the invention in the region of the hollow injection needle, whereby a fashioning of the injection channels modified in comparison to FIG. 4 is provided.

Two injection channels 13, 14 are formed in the embodiment of FIG. 5 in that an axially proceeding partition 16 is bonded into the hollow injection needle 3, so that the two injection channels 13 and 14 proceed at the two sides of the partition. They each respectively discharge into one of the hose channels of a two-lumen hose 17 fixed to the sleeve 8 but can also be connected to hoses having different diameters as in the above-described embodiments, whereby the hose having the smaller diameter is laterally inserted into that having the larger diameter. The partition 16 is placed such that it ends in the ground plane 30 of the hollow injection needle 3. The components to be brought into reaction meet immediately upon emergence from the hollow needle and are blended with one another.

Further embodiments of the present invention are possible by employing individual hollow needles; it must be merely assured that the individual hollow needles end in a common ground plane. As a result thereof, the angle of the tip for a low puncture resistance is as small as that of every individual hollow needle; the blending of the ejected components is also promoted.

Figure 6:
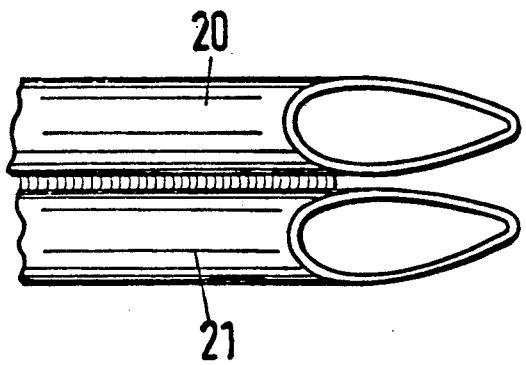
FIG. 6 a plan view onto a further embodiment of the invention in the region of the hollow injection needle.
Figure 7:
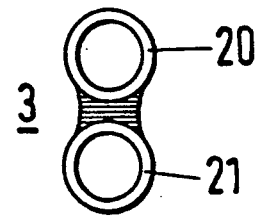
FIG. 7 a cross section through the hollow injection needle of FIG. 6.
Figure 8:
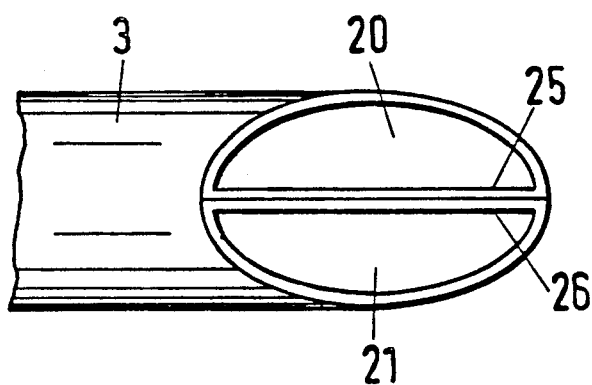
FIG. 8 the plan view of a modified fashioning of the hollow injection needle.

In FIG. 6, the individual hollow needles 20, 21 are placed against one another in parallel and are inseparably joined to one another in their adjacent region, for example are bonded to one another. FIG. 7 shows a cross section through the hollow injection needle 3 formed in this way, whereby the overall cross section is formed of those of the individual hollow needles 20, 21 each of which has a circular cross section.

The individual hollow needles 20, 21 shown in FIG. 7 that form the hollow injection needle 3 with one another each comprise respective flat sides 25, 26 that are placed against one another and along which the individual hollow needles 20, 21 are secured to one another.

Figure 9:
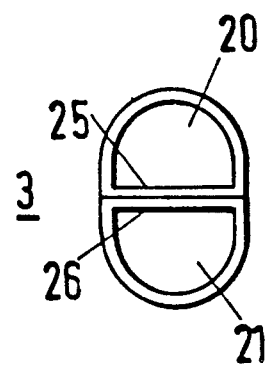
FIG. 9 a cross section through the hollow injection needle of FIG. 8.
Figure 10:
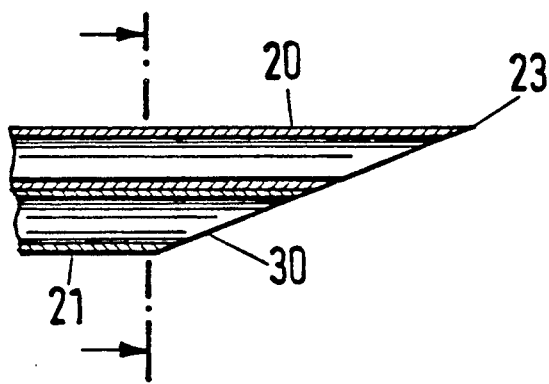
FIG. 10 a longitudinal section through a hollow injection needle conforming to a further embodiment of the invention.
Figure 11:
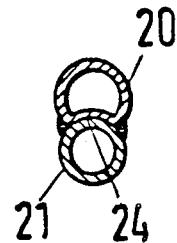
FIG. 11 a cross section through the hollow injection needle of FIG. 10.

The cross-sectional areas of the individual hollow needles, as shown in FIG. 9, are semicircular, so that the overall cross section of the hollow injection needle 3 is essentially circular. According to FIG. 10, the hollow injection needle 3 is again composed of two individual hollow needles 20, 21, whereby one of the individual hollow needles 20 has one side provided with a longitudinally proceeding, channel-shaped inwardly arced portion 24 into which the other individual hollow needle 21 is introduced. FIG. 11 shows this arrangement in cross section. The beveled surfaces of the two individual hollow needles 20, 21 lie in a common ground plane 30 that, for forming the tip 23 of the needle, is placed at an angle of 15° through 25°, preferably 20°, with reference to the axis of the injection needle 3.

Figure 12:
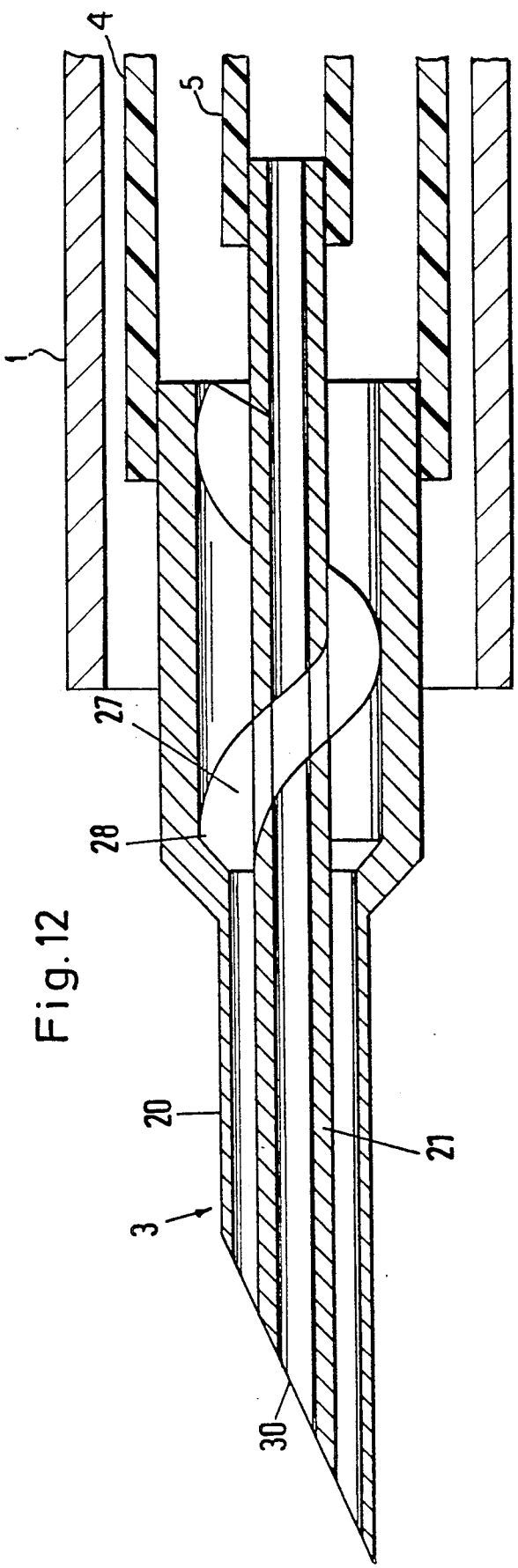
FIG. 12 a partial longitudinal section through an embodiment of the present invention in the region of the hollow injection needle, whereby the individual hollow needles are coaxially arranged.

FIG. 12 shows an embodiment of the hollow injection needle 3 for an injection means of the present invention wherein two individual hollow needles 20, 21 are placed such coaxially that their discharge surfaces discharge in a common plane 30. The inwardly disposed individual hollow needle 21 is thereby fixed with reference to the outer individual hollow needle 20 by a helically proceeding rib 27 that engages into corresponding grooves 28 at at least three locations at the inside wall of the outer individual hollow needle 20. Other fastening possibilities are also conceivable when it is merely assured that the inner individual hollow needle 21 retains its position with reference to the outer individual hollow needle 20.

Both individually as well as in arbitrary combinations, the features of the invention disclosed in the above specification, in the drawings as well as in the claims can be critical for the realization of the various embodiments of the invention.

Although other modifications and changes may be suggested by those skilled in the art, it is the intention of the inventors to embody within the patent warranted hereon all changes and modifications as reasonably and properly come within the scope of their contribution to the art.

We claim:

1. An injection apparatus for injecting at least two components to be brought into reaction with one another, comprising:

a hollow injection needle having a discharge plane from which the at least two components are discharged, said hollow injection needle including a tube mounted therein having a discharge end from which a first of said at least two components is discharged, said tube being mounted substantially coaxial of a distal end of said hollow injection needle so that said needle defines injection channels for said at least two components within said hollow injection needle;

a plurality of coupling connections corresponding in number to the number of the at least two components, said coupling connections being in fluid communication with said hollow injection needle through a corresponding plurality of hoses so that the at least two components are dischargeable from said hollow injection needle by input at said coupling connections;

said corresponding plurality of hoses each respectively connected between one of said coupling connections and said hollow injection needle so that the at least two components discharge in the common plane whereat the reaction of the at least two components is initiated;

a catheter arranged coaxially about said corresponding plurality of hoses and having a grip member at an end, said grip member of said catheter being at ends of said corresponding plurality of hoses that are connected to said plurality of coupling connections.

2. An injection apparatus according to claim 1, wherein said plurality of hoses is a first hose and a second hose, the hollow injection needle being connected to said first hose, said second hose having a smaller outside diameter than an inside diameter of the first hose, said second hose extending coaxially in said first hose up to the grip member, the second hose discharging at a slight distance preceding a proximal end of the hollow injection needle.

3. An injection apparatus according to claim 1, wherein said injection channels correspond in number to the number of components, said injection channels discharging in the discharge plane of the injection needle, said tube defining a first of said plurality of injection channels.

4. An injection apparatus according to claim 3, wherein said plurality of injection channels include first and second injection channels, and said plurality of hoses being first and second hoses, the first injection channel being connected to the first hose, the second hose being connected to the second injection channel, said first hose having a smaller outside diameter than an inside diameter of the second hose, said first hose proceeding up to the gripping member.

5. An injection apparatus according to claim 1, wherein the hollow injection needle comprises a plurality of individual hollow needles corresponding in number to the number of components, said tube being connected to a first of said individual hollow needles, end planes of said individual hollow needles lying in a common plane.

6. An injection apparatus according to claim 5, wherein the individual hollow needles have mutually different diameters.

7. An injection apparatus according to claim 5, wherein the individual hollow needles are attached such to one another that a tip of the hollow injection needle is formed by a tip of the individual hollow needle having a largest diameter.

8. An injection apparatus for injecting at least two components to be brought into reaction with one another, comprising:
   a hollow injection needle having a discharge plane from which the at least two components are discharged, said hollow injection needle comprises a plurality of individual hollow needles corresponding in number to the number of components, end planes of said individual hollow needles lying in a common plane, the individual hollow needles being arranged coaxially relative to one another;
   a plurality of coupling connections corresponding in number to the number of components, said coupling connections being in fluid communication with said hollow injection needle so that the at least two components are dischargeable from said hollow injection needle by connection to said coupling connections;
   a catheter arranged coaxially about a corresponding plurality of hoses and having a grip member at a first end, the coupling connections are provided at the grip member of the catheter;
   said corresponding plurality of hoses each respectively connected between one of the coupling connections and one of individual said hollow needles so that the components discharge in the common plane wherein the reaction of the components is initiated.

* * * * *